(12) United States Patent
Freidberg et al.

(10) Patent No.: US 6,929,658 B1
(45) Date of Patent: Aug. 16, 2005

(54) STENT WITH COVER CONNECTORS

(75) Inventors: Carlos Vonderwalde Freidberg, Richmond (CA); Daniel Capuano, Huixquilucan (MX)

(73) Assignee: Design & Performance-Cyprus Limited, Nicosia (CY)

( * ) Notice: Subject to any disclaimer, the term of this patent is extended or adjusted under 35 U.S.C. 154(b) by 0 days.

(21) Appl. No.: 09/522,336

(22) Filed: Mar. 9, 2000

(51) Int. Cl.[7] .................................. A61F 2/06
(52) U.S. Cl. ..................................... 623/1.13
(58) Field of Search .............. 623/1.1, 1.12–1.17, 623/1.23, 1.25, 1.32, 1.36, 1.35; 606/194, 606/195

(56) References Cited

U.S. PATENT DOCUMENTS

| | | | |
|---|---|---|---|
| 5,607,444 A | 3/1997 | Lam | 606/194 |
| 5,667,523 A | 9/1997 | Bynon et al. | 606/198 |
| 5,709,713 A | 1/1998 | Evans et al. | 623/1 |
| 5,755,778 A * | 5/1998 | Kleshinski | 623/1.13 |
| 5,769,882 A | 6/1998 | Fogarty et al. | 623/1 |
| 5,769,887 A | 6/1998 | Brown et al. | 623/1 |
| 5,782,904 A | 7/1998 | White et al. | 623/1 |
| 5,824,054 A * | 10/1998 | Khosravi et al. | 623/1.44 |
| 5,851,228 A * | 12/1998 | Pinheiro | 623/1.13 |
| 5,865,723 A | 2/1999 | Love | 600/36 |
| 5,897,589 A | 4/1999 | Cottenceau et al. | 623/1 |
| 5,935,161 A | 8/1999 | Robinson et al. | 623/1 |
| 6,042,605 A | 3/2000 | Martin et al. | |
| 6,099,559 A | 8/2000 | Noting | |
| 6,117,166 A * | 9/2000 | Winston et al. | 623/1.13 |
| 6,168,619 B1 | 1/2001 | Dinh et al. | 623/1.13 |
| 6,235,054 B1 | 5/2001 | Berg et al. | 623/1.36 |
| 6,248,116 B1 * | 6/2001 | Chevillon et al. | 128/898 |
| 6,254,627 B1 * | 7/2001 | Freidberg | 606/195 |
| 6,325,820 B1 * | 12/2001 | Khosravi et al. | 623/1.13 |

FOREIGN PATENT DOCUMENTS

| | | |
|---|---|---|
| EP | 0732089 | 9/1996 |
| EP | 0960607 | 12/1999 |
| WO | WO9944536 | 9/1999 |

* cited by examiner

*Primary Examiner*—(Jackie) Tan-Uyen T. Ho
(74) *Attorney, Agent, or Firm*—G.E. Ehrlich (1995) Ltd.

(57) ABSTRACT

A stent for maintaining the patency of a bodily lumen has a tubular body with at least one cover connector integrally formed on the tubular body.

15 Claims, 7 Drawing Sheets

STENT WITH COVER CONNECTORS

BACKGROUND OF THE INVENTION

This invention relates to the field of intraluminal support devices such as stents and the like. Typically, stents are expandable, tubular metallic devices that are positioned within a patient's vasculature or other body lumen and expanded in order to support a vessel or body lumen at a desired intraluminal location to allow the flow of blood or other body fluids therethrough. Often, the stents are formed from a deformable metal and delivered to the desired intraluminal location by mounting the stent onto an expandable portion, e.g. a balloon, on the distal extremity of a delivery catheter. By advancing the catheter through the body lumen, the stent may be delivered to a desired position and expanded therein by expanding the balloon to an expanded configuration, seating it within the artery or other body lumen. Other implementations make use of a self-expanding stent formed from a suitable material such as pseudoelastic material that is delivered in a constricted condition and when released spontaneously expands to an enlarged configuration. In other embodiments, a stent made of shape memory alloy (e.g. NiTi alloy) may be inserted into the body lumen in a martensitic phase and transformed to an austenite phase which has an expanded memory when raised to a temperature above the transformation temperature, usually less than 45° C. Further details of stents and stent delivery systems may be found in U.S. Pat. No. 5,507,768 (Lau et al.), U.S. Pat. No. 5,458,615 (Klemm et al.), and U.S. Pat. No. 5,514,154 (Lau et al.), incorporated herein by reference in their entireties.

Stents are often used in conjunction with an intravascular treatment for conditions such as obstructive coronary artery disease and peripheral artery disease. For example, ablation, atherectomy, balloon dilation, laser treatment or other procedures are among the methods used to widen a stenotic region of a patient's vasculature. However, restenosis occurs in large percentage of percutaneous transluminal coronary angioplasty (PTCA) patients and rates can be even higher with other procedures. Restenosis is thought to be a natural healing reaction provoked by injury from the intravascular procedure. The healing process frequently causes thrombosis and may lead to intimal hyperplasia that occludes the vessel. The prior art has employed a number of mechanical and pharmacological strategies to reduce the restenosis rate, but none have been particularly effective. Accordingly, stents have been proposed to maintain the patency of a treated vessel and prevent restenosis. Using stents, restenosis rates have fallen to less than 20%. Although helpful in reducing restenosis, stents do not represent a complete solution. The framework of the stent may still allow migration and proliferation of the smooth muscle cells, while the stent itself can be thrombogenic. To address these problems, stents have been provided with covers made from various materials such as DACRON, polytetrafluoroethylene (PTFE), heterologous tissue and autologous veins, arteries and tissue.

It would be a significant advance to provide a stent with an improved connector for securing a cover to the stent. This invention satisfies these and other needs.

SUMMARY OF THE INVENTION

The invention is directed to a stent suitable for maintaining the patency of a bodily lumen, generally comprising a tubular body and at least one cover connector on the tubular body. A stent assembly of the invention generally comprises a stent having cover connectors in contact with a cover to secure the cover to a surface of the stent. The invention also comprises methods of securing a cover to a stent.

In a first embodiment, the cover connector on an expandable tubular body has a first section, a second section, and a third section between the first and second sections. The connector has an open configuration, and a closed configuration in which the first section has at least one bend and the second section has at least one bend, so that the first and second sections are bent together and are directed towards the third section therebetween. The ends of the connector are configured to pierce the cover so that at least a portion of the first and second sections extend through the cover. With the cover pierced by the first and second ends of the connector, the ends of the connector are bent together towards the third section, so that the first and second sections of the connector are adjacent an outer surface of the cover and the third section of the connector is adjacent an inner surface of the cover, to form the closed configuration. A stent assembly of the invention generally comprises a covered stent having at least a portion of the first and second sections of the cover connector extending through a cover, to secure the cover to the stent. In one embodiment the cover connector is configured to draw the lengthwise edges of a stent cover together as the connector is bent from the first to the second configuration to close the cover about the stent surface.

A method of securing a cover to a stent generally comprises piercing the first end of the cover connector at a first location on the cover and piercing the second end of the cover connector through the cover at a second location from an inner surface to an outer surface of the cover. The first and second sections of the cover connector are bent towards the third section to form the closed configuration and secure the cover to the stent.

In a second embodiment, the cover connector presses the cover against a surface of the stent to secure the cover thereto without piercing the cover. The cover connector is secured to an end of the expandable tubular body of the stent, and is configured to fold from an open configuration to a closed configuration in which the connector extends toward a midpoint of the tubular body between the first and second ends of the tubular body and contacts a cover located between the cover connector and a surface of the tubular body of the stent, to secure the cover thereto. The cover connector presses the cover against a surface of the stent to secure the cover thereto without piercing the cover. A method of securing a cover to a stent generally comprises placing a cover on the stent and folding the cover connector from the open configuration to the closed configuration so that at least a section of the cover is in contact with the cover connector and between the cover connector and a surface of the stent.

The cover connectors may be configured to secure a cover to either an inner surface or an outer surface of the tubular body of the stent. In a presently preferred embodiment, a plurality of cover connectors are provided on the stent to connect a cover which extends over a substantial portion, and preferably all of the length of the stent, in order to minimize restenosis in the body lumen.

In one embodiment, a stent is provided with eyelet members having an opening therein configured to receive a securing member such as a suture to thereby secure a cover to the stent.

The cover may be a variety of suitable materials which are preferably expandable, biocompatible, and non-thrombogenic, including autologous tissue, heterologous tissue such as bovine pericardium, porcine pericardium, aortic leaflet, and polymeric materials such as PTFE and polyesters such as DACRON. In a preferred embodiment, the cover is generally cylindrical for corresponding to the tubular framework or the stent.

The stent may be an expandable, tubular framework and may be a conventional self expanding or balloon expandable stent. A variety of stent designs may be used, including stents formed from braided tube, slotted tubes, and coils or closed sinusoidal rings of wire or ribbon, and the like.

The stent assembly is implanted in the patient's body lumen, typically by mounting the stent assembly on the distal extremity of a delivery catheter. Specifically, a tubular stent with a cover disposed about at least part of the stent, and secured thereto by the cover connectors, is mounted on a balloon, for a balloon expandable stent, or on a containing mechanism for a self expandable stent. The catheter is advanced through the body lumen within the patient until the distal extremity of the catheter having the stent assembly is positioned at a desired location therein. The stent assembly is expanded by expanding the balloon or releasing the containing mechanism on which the stent assembly is mounted to anchor the stent assembly within the body lumen. Once the stent assembly is effectively positioned within the body lumen, the expanded balloon may be contracted, e.g. by deflation, and then the delivery catheter may be withdrawn.

The stent having cover connectors of the invention provides for easy attachment of a stent cover onto the stent. This is particularly advantageous in the case of a cover which is impregnated with a therapeutic or diagnostic agent, such as an angiogenesis or antithrombotic agent, just before use or stored in the agent to preimpregnate the cover. The cover connectors allow the impregnated cover to be quickly and easily attached to the stent just before implantation of the stent assembly in the patient's body lumen. Thereafter, the stent assembly can be positioned at a desired site within the patient's body lumen, where the cover will release the therapeutic agent.

The cover connectors of the invention provide for improved connection of a cover to a stent surface, by providing an easily formed connection between the cover and the stent. The cover connectors of the invention avoid the use of sutures or adhesive to secure the cover to the stent, yet provide a durable, rugged, low profile connection. These and other advantages of the invention will become more apparent from the following detailed description and exemplary figures.

DETAILED DESCRIPTION OF THE INVENTION

Figure 1:
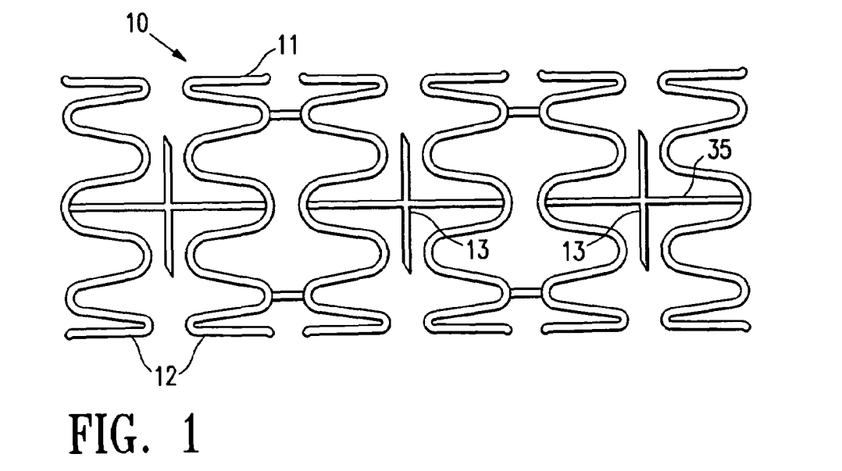
FIG. 1 is an elevational view of a stent having cover connectors which embodies features of the invention.
Figure 2:
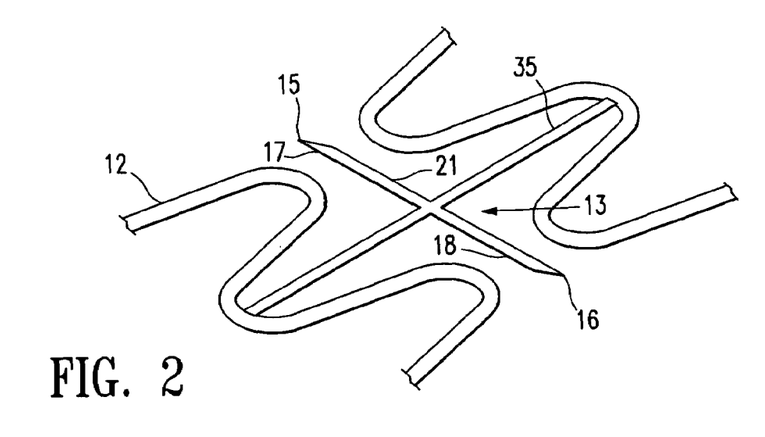
FIG. 2 is an enlarged view of the stent shown in FIG. 1, illustrating the cover connector in an open configuration.
Figure 3:
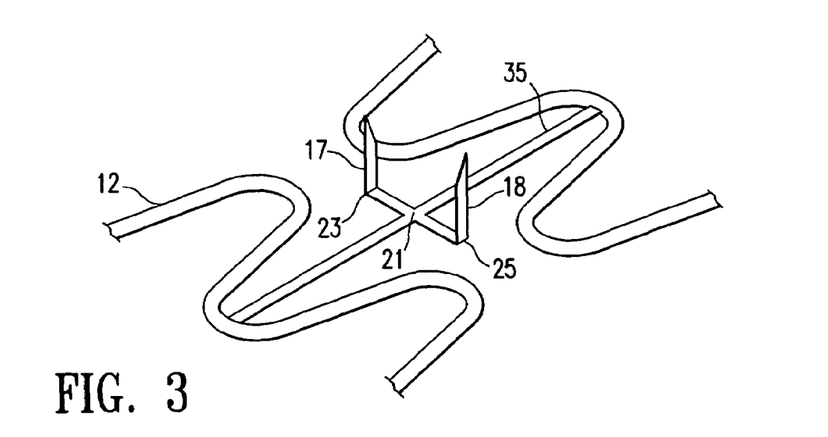
FIG. 3 illustrates the cover connector shown in FIG. 2, in a bent U-shaped configuration.
Figure 4:
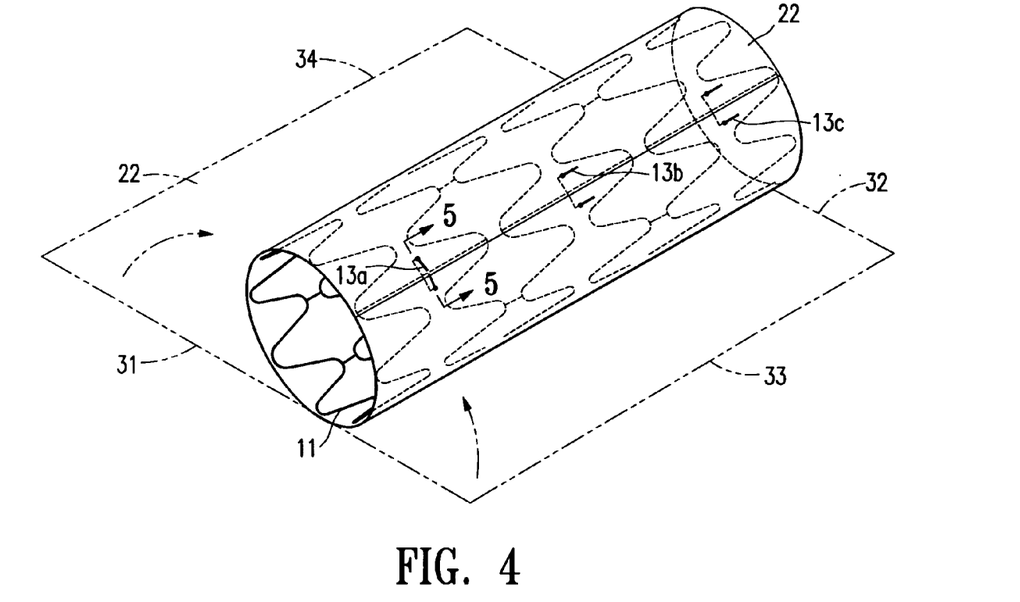
FIG. 4 is a perspective view, partially in phantom, of a stent assembly which embodies features of the invention illustrating a cover secured to the stent.
Figure 5:
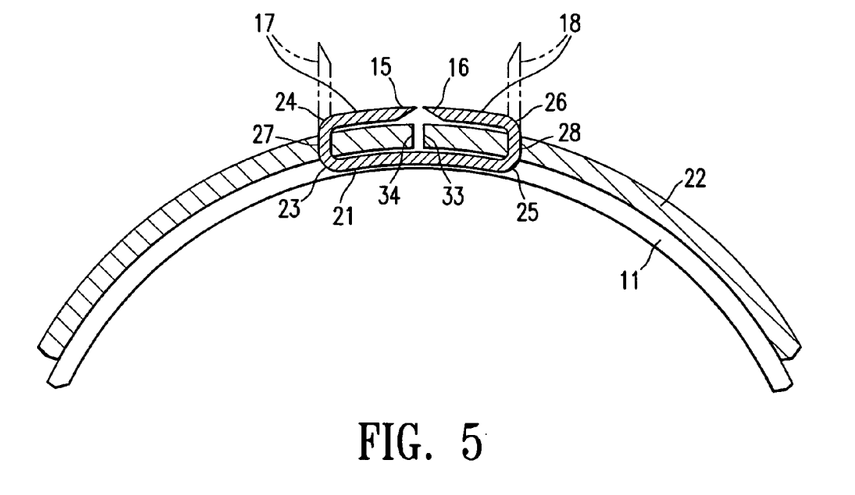
FIG. 5 is a transverse cross sectional view of the stent assembly shown in FIG. 4, taken along lines 5—5.

FIG. 1 is an elevational view of a first embodiment of a stent 10 which embodies features of the invention, comprising an expandable tubular body 11 having first and second ends, a lumen therein, and a framework of spaced apart wall sections 12 defining an open-walled structure, and cover connectors 13 on the tubular body. The cover connectors 13, which are illustrated in more detail in FIG. 2, showing an enlarged view of the connectors shown in FIG. 1, have a first end 15, a second end 16, a first section 17 adjacent to the first end 15, a second section 18 adjacent to the second end 16, and a third section 21 between the first and second sections. The connector 13 is illustrated in FIG. 2 in an open configuration in which the connector is a generally straight, pointed projection attached to the tubular body. FIG. 3 illustrates the connector shown in FIG. 2 bent into a generally U-shaped configuration which facilitates piercing the ends of the connector through a cover to be secured to the stent. The connector is bent at a first location (forming bend 23) on the first section so that at least a section of the first section is above the tubular body, and at a first location (forming bend 25) on the second section so that at least a section of the second section is above the tubular body. FIG. 4 illustrates a cover 22 pierced by the ends of the cover connector. As best illustrated in FIG. 5, showing a transverse cross section of the stent assembly shown in FIG. 4, taken along lines 5—5, the cover connector assumes the closed configuration as the first section 17 and the second section 18 are bent so that at least a portion of the first and second sections are in contact with the outer surface of the cover and the third section 21 is adjacent the inner surface of the cover. In the presently preferred embodiment illustrated in FIG. 5, the cover connector assumes the closed configuration when the first section has a first bend 23 and a second bend 24 in the same direction as the first bend in the first section, and the second section has a first bend 25 and a second bend 26 in the same direction as the first bend in the second section. However, the closed configuration can be formed by a single bend in the first section and a single bend in the second section when the angle of the bend is large enough that the first and second sections contact the outer surface of the cover (not shown).

In the embodiment illustrated in FIG. 5, the second bend 24 on the first section is between the first end 15 of the connector and the first bend 23 on the first section, and the second bend 26 on the second section is between the second end 16 of the connector and the first bend 25 on the second section. In an alternative embodiment in which the connector is configured to draw the edges of the cover together as the connector is bent into the closed configuration, the second bend 24 on the first section is between the third section 21 of the connector and the first bend 23 on the first section, and the second bend 26 on the second section is between the third section 21 of the connector and the first bend 25 on the second section. Thus, with the connector in the U-shaped configuration illustrated in phantom in FIG. 5 and the cover pierced by the first and second ends of the connector, as the connector is bent at the second location on the first and second sections to form the second bend 24, the cover will be stretched about the stent and the edges of the cover pushed together or further around the stent. Similarly, in the embodiment illustrated in FIG. 5, a portion 27 of the first section between the first and second bends thereon is directed perpendicular to the third section, and a portion 28 of the second section between the first and second bends thereon is directed perpendicular to the third section. In an alternative embodiment (not shown), after the cover 22 is placed on the connector, the portion 27 between the first and second bends on the first section and the portion 28 between the first and second bends on the second section are disposed at an angle toward the third section 21 by further bending the first bends 23 and 25 from a perpendicular angle to an acute angle, so that the edges of the cover are pushed or drawn together.

Figure 6:
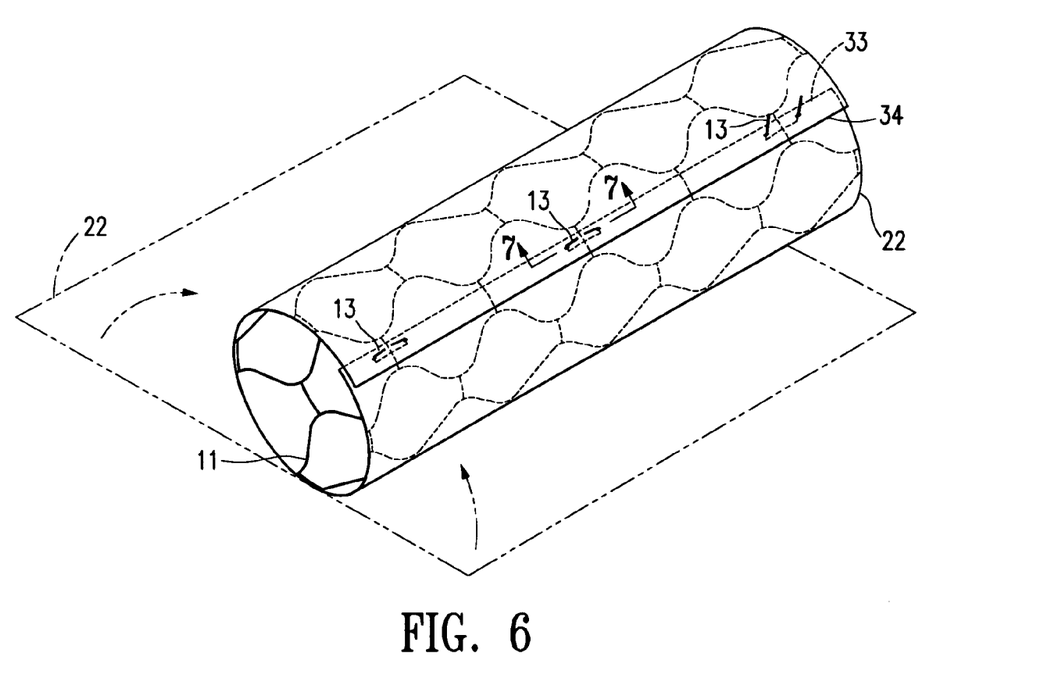
FIG. 6 is a perspective view, of an alternative embodiment of a stent assembly which embodies features of the invention, in which the cover connector is axially aligned in the open configuration with the longitudinal axis of the stent
Figure 7:
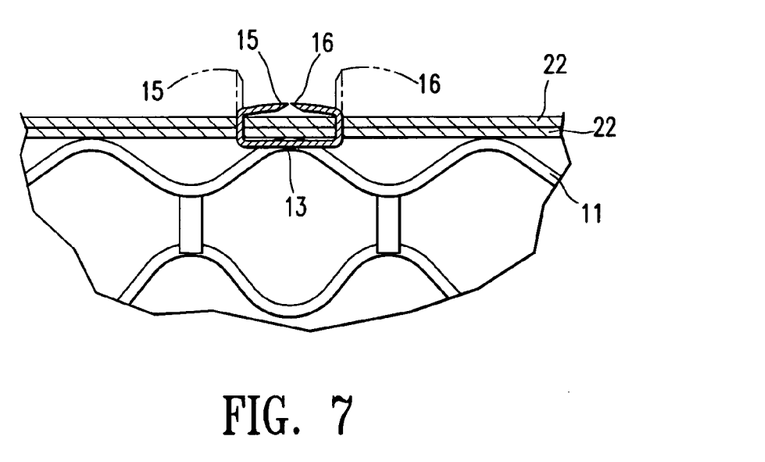
FIG. 7 is longitudinal cross sectional view of a section of the stent assembly shown in FIG. 6, taken along lines 7—7.

In FIG. 4, a first cover connector 13a is in the closed configuration, and cover connectors 13b and 13c are in the U-shaped configuration. FIG. 4 illustrates the cover 22 in phantom before being wrapped around the stent and connected thereto by the cover connectors 13. The cover 22 is in the form of a sheet of material wrapped around the stent, with a first end 31 and a second end 32, and first 33 and second 34 edges extending the length of the cover from the first to the second end thereof. In the presently preferred embodiment illustrated in FIG. 5, the two edges 33/34 of the cover corresponding to the length of the cover are abutting. However, in an alternative embodiment the edges may overlap one another as illustrated in FIGS. 6 and 7. Additionally, although the cover is illustrated as a sheet of material wrapped around the stent, the cover could be preformed into a tubular cylinder before being placed on the stent and connected thereto.

In one embodiment, the connector is optionally provided with weakened sections configured to bend, as for example by thinning or narrowing the connector at the locations configured to bend. The connector 13 has a length that is typically about 0.15 mm to about 10 mm, preferably about 0.5 mm to about 4 mm, and a width that is about 0.07 mm to about 2 mm, preferably about 0.1 mm to about 1 mm. The first and second sections have a length of about 0.1 to about 6 mm, preferably about 0.33 to about 2.6 mm. The third section has a length of about 0.05 to about 4 mm, preferably about 0.17 to about 1.4 mm.

The cover connectors may be secured to the tubular body in a variety of configurations. In the presently preferred embodiment of the invention shown in FIG. 1, the cover connector 13 is attached to a support member 35 extending between the spaced apart wall sections of the tubular body of the stent. The support member has a first end secured to the tubular body and a second end secured to the tubular body, and the third section of the connector is secured to the support member between the first and second ends of the support member. The cover connectors may be manufactured as a separate part and later joined to the tubular body, or manufactured with the tubular body as a one piece unit. The terms "secured" and "attached" as used herein to discuss the connection between the cover connectors and the tubular body should be understood to include cover connectors separately joined to the tubular body and cover connectors made as a section of the tubular body.

In a presently preferred embodiment, the connector has a longitudinal axis which is not axially aligned with the tubular body longitudinal axis. As a result, the connector can be used to secure the two edges 33/34 of the cover without the need for preattaching the edges 33/34 of the cover together to form a cylinder, or without overlapping the edges of the cover. In the presently preferred embodiment illustrated in FIG. 1, the cover connector is substantially perpendicular to the longitudinal axis of the tubular body of the stent in the open configuration. By substantially perpendicular, it should be understood that the angle the cover connector makes relative to the longitudinal axis may be 90° or somewhat different from a 90° angle, as for example by about 65° to about 115°. However, in an alternative embodiment, the cover connector may have a longitudinal axis axially aligned with the tubular body longitudinal axis. FIG. 6 and illustrate a cover connector which is directed substantially parallel to the longitudinal axis of the tubular body in the open configuration. As illustrated in FIG. 6 showing the stent with a cover being secured thereto, and FIG. 7 showing a cross section of the assembly shown in FIG. 6 taken along lines 7—7, the edges of the cover 22 are overlapping so that sections of cover adjacent to the opposite edges of the stent can be pierced by the first and second ends of the connector to secure the cover to the stent.

Figure 8:
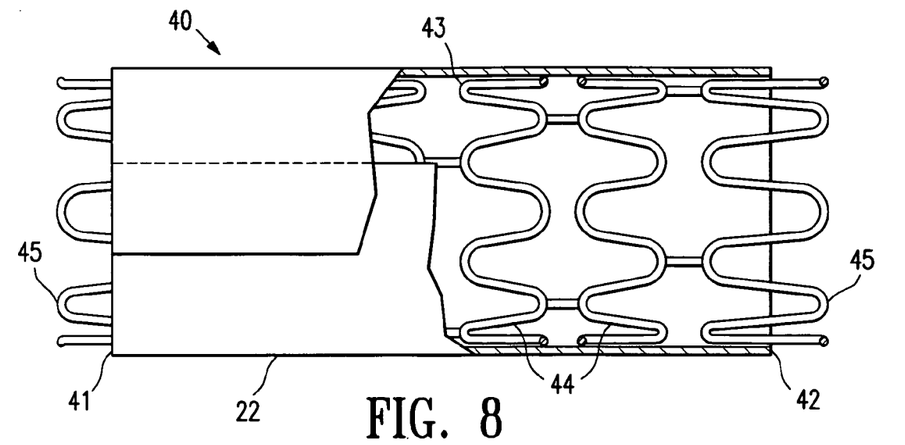
FIG. 8 is an elevational view, partially broken away and partially in section, of an alternative embodiment of a stent assembly which embodies features of the invention, having cover connectors in an open configuration on the ends of the stent.
Figure 9:
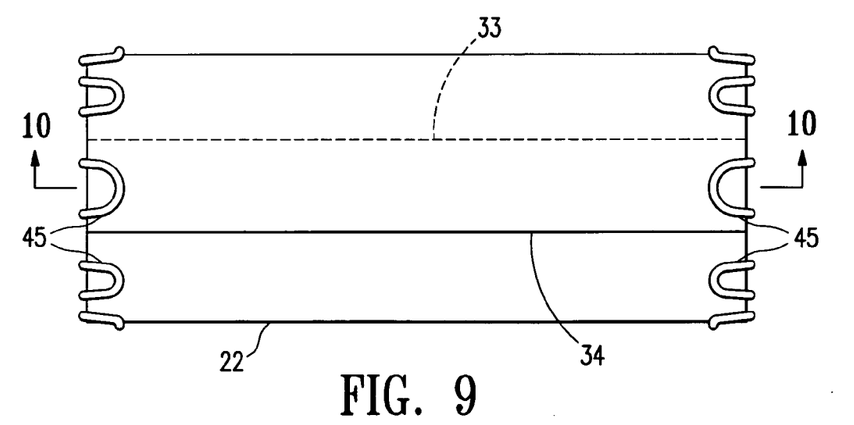
FIG. 9 is an elevational view of the stent assembly shown in FIG. 8, illustrating the cover connectors in a closed configuration.
Figure 10:
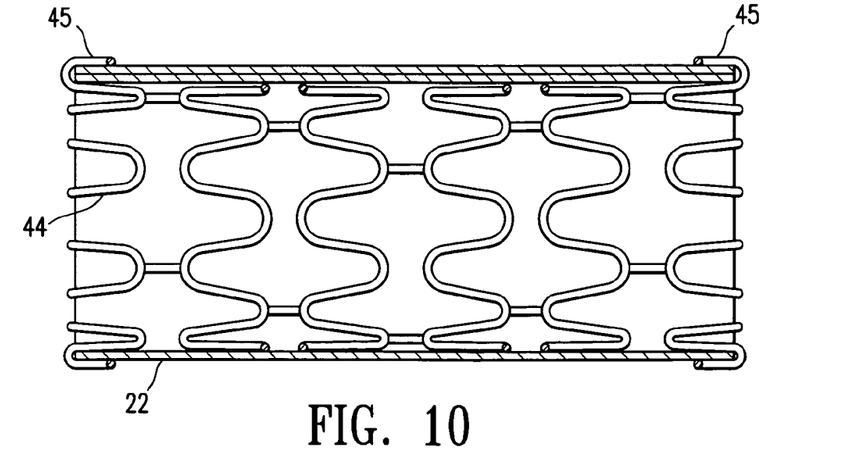
FIG. 10 is a longitudinal cross sectional view of the stent assembly shown in FIG. 9, taken along lines 10—10.

FIG. 8 illustrates an alternative embodiment of a stent 40 embodying features of the invention, comprising an expandable tubular body having a first end 41, a second end 42, and a midpoint 43 therebetween, and a framework of spaced apart, wall sections 44 defining an open-walled structure. The stent 40 has at least one cover connector 45 secured to an end of the tubular body. The cover connector 45 has an open configuration, and a closed configuration in which the connector extends toward the midpoint of the tubular body, and is configured to fold from the open configuration to the closed configuration to contact a cover 22 located between the cover connector and a surface of the stent. In the embodiment illustrated in FIG. 8, the stent has a plurality of cover connectors secured about a circumference of the first end and the second end of the tubular body of the stent. FIG. 9 illustrates the cover connectors 45 in the closed configuration in which the cover connector is folded so that at least a section of the cover 22 is between the cover connector and the outer surface of the stent with an outer surface of the cover 22 in contact with the cover connector. As best illustrated in FIG. 10 showing a longitudinal cross section of the assembly shown in FIG. 9 taken along lines 10—10, the connectors 45 are folded in the closed configuration so that they have a surface which is substantially parallel to a surface of the tubular body for maximum contact with the cover. By substantially parallel, it should be understood that the surface of the cover connectors 45 adjacent to the cover is completely or nearly completely in contact with the cover. As illustrated in FIG. 10, the edges 33/34 of the cover 22 extending the length of the cover are overlapping. However, in an alternative embodiment (not shown), the edges of the cover are abutting. In this embodiment, one cover connector 45 preferably contacts both edges of the cover to hold the two edges securely together. One or more of the cover connectors 13 may be provided on stent 40, together with cover connectors 45. In one embodiment, the cover connectors 13 are provided on the ends of stent 40 together with cover connectors 45.

In the embodiment illustrated in FIG. 8, the connector 45 is a closed loop, and is formed by a wire or ribbon, which provides for optimal surface contact between the cover and the cover connector without forming a disadvantageous barrier between the cover and the vessel wall in which the stent assembly will be implanted. However, it would be obvious that a variety of other suitable shapes may be used including discs, fingers or projections, and the like. The cover connector 45 has a length that is typically about 0.5 mm to about 10 mm, preferably about 1 mm to about 4 mm, and a width that is about 0.07 mm to about 2 mm, preferably about 0.1 mm to about 2 mm. The width of the wire or ribbon forming the connector in FIG. 8 is about 0.1 mm to about 1 mm.

Figure 11:
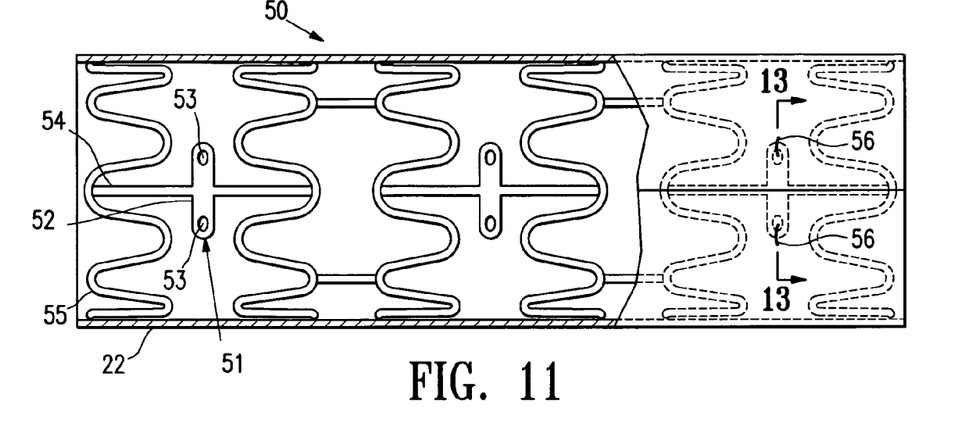
FIG. 11 is an elevational view, partially in longitudinal cross section, of a stent assembly which embodies features of the invention, having eyelet members comprising a body having eyelets in opposite ends of the body, the body being attached to a support member, and having sutures in the eyelet members connecting the cover to the stent.
Figure 13:
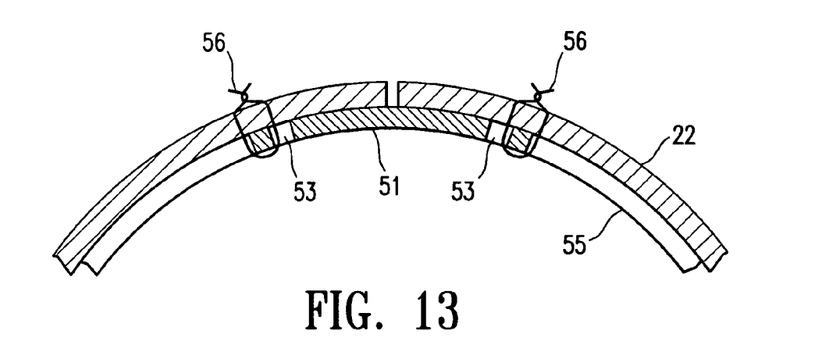
FIG. 13 is a transverse cross sectional view of the eyelet members shown in FIG. 11, taken along line 13—13.

FIG. 11 illustrates an alternative embodiment of a stent assembly 50 which embodies features of the invention, having eyelet members 51 comprising an elongated body 52 having one or more eyelets or openings 53 in opposite ends of the body 52. The body 52 is attached to a support member 54 which extends across adjacent coiled sections of stent 55. The openings 53 are configured to receive a securing member, to thereby connect cover 22 to stent 55. A variety of suitable securing members may be used including sutures, staples, hooks, and wires. In the embodiment illustrated in FIG. 11, sutures 56 are in the openings 53 to connect the cover to the stent. FIG. 13 is a transverse cross sectional view of the eyelet member 51 shown in FIG. 11, taken along line 13—13, illustrating a suture 56 in each opening 53 with knotted ends to connect cover 22 to stent 55.

Figure 12:
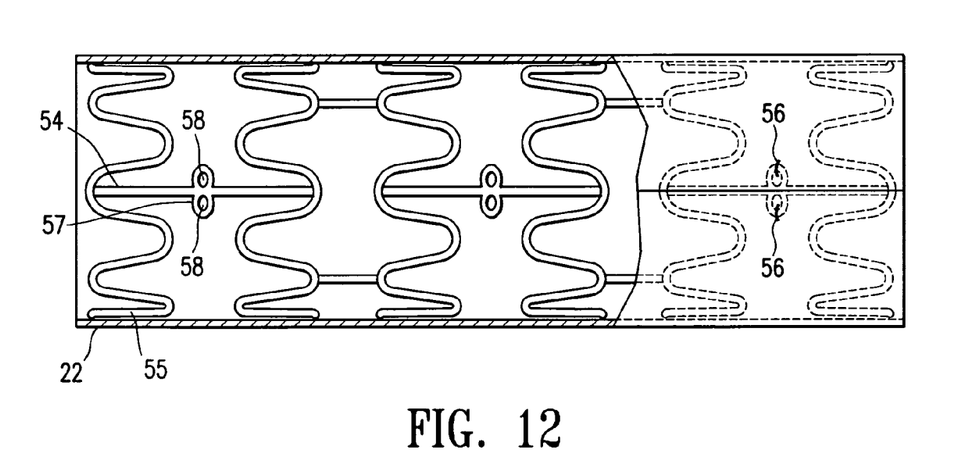
FIG. 12 is an elevational view, partially in longitudinal cross section, of an alternative embodiment of a stent assembly which embodies features of the invention having eyelet members attached to a support member, and having sutures in the eyelet members connecting the cover to the stent.

In an alternative embodiment of a stent assembly which embodies features of the invention, illustrated in FIG. 12, eyelet members 57 attached to support member 54 comprise openings 58 on either side of the support member 54, so that each opening 58 is directly adjacent to the support member 54. Sutures 56 in each opening 58 connect the cover 22 to the stent 55.

Figure 14:
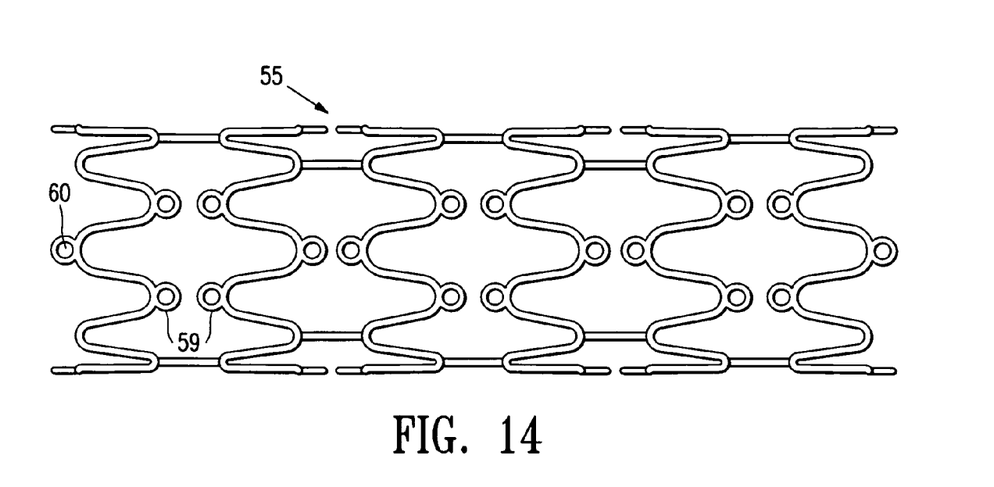
FIG. 14 is an elevational view of a stent having eyelet members comprising closed rings or loops attached to the stent, which embodies features of the invention.
Figure 15:
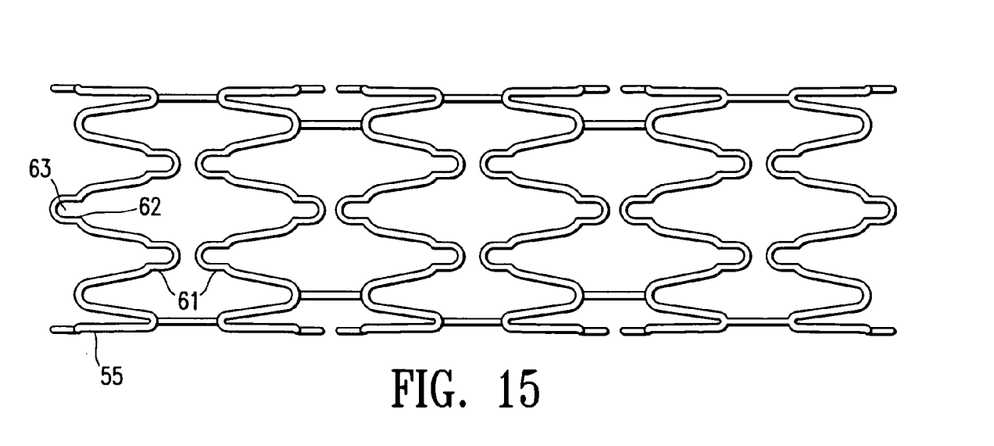
FIG. 15 is an elevational view of a stent having eyelet members comprising open rings or lopes attached to the stent, which embodies features of the invention.

FIG. 14 illustrates an alternative embodiment of a stent 55 having eyelet members 59 comprising closed rings or loops attached to the stent, which embodies features of the invention. The eyelet members 59 extend from the side of the stent 55 on the ends of the sinusoidal turns of the stent, with a central opening 60 configured to receive suture 56 or other securing member, to connect the cover 22 to the stent 55. In an alternative embodiment, eyelet members 61 are open rings or loops, as for example with an aperture 62 adjacent to the edge of the turns of the stent 55 and with an opening 63 configured to receive suture 56 or other securing member, illustrated in FIG. 15. In the embodiment of FIGS. 14 and 15, eyelet members 59 and 61 are on the top outer edge of adjacent sinusoidal turns of the stent 55. However, in alternative embodiments the eyelet members may be provided on nonadjacent turns of the stent 55 as for example on alternate turns.

Figure 16:
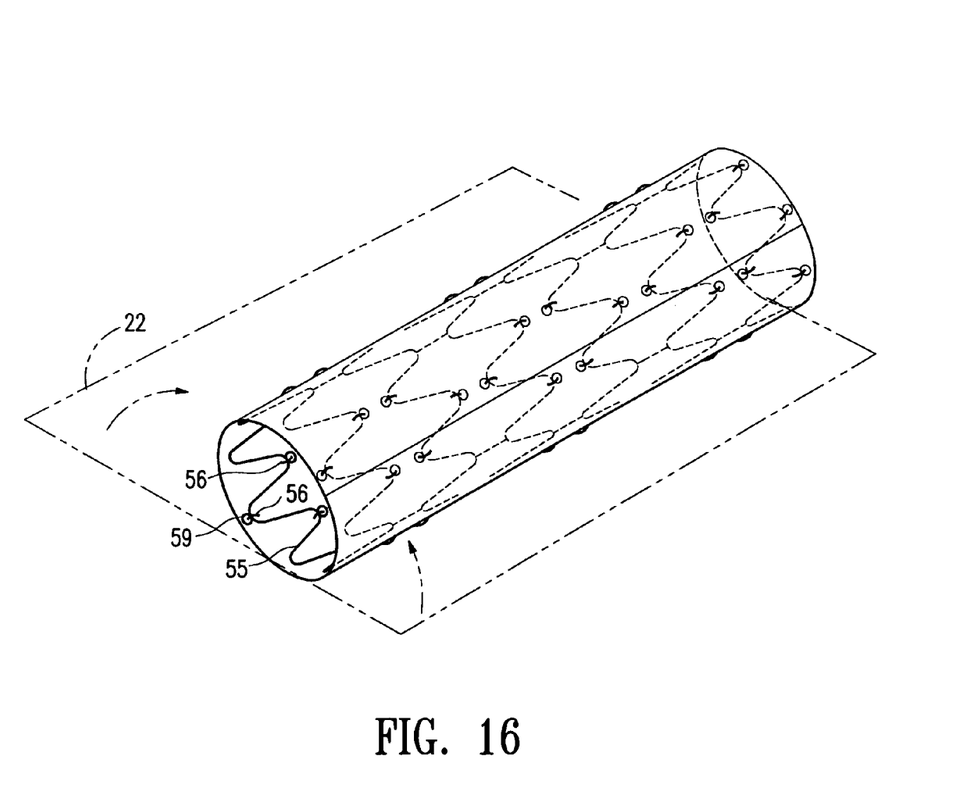
FIG. 16 is a perspective view, partially in phantom, of a stent assembly which embodies features of the invention, illustrating a cover secured to the stent by sutures in eyelet members attached to the stent.

In a presently preferred embodiment, eyelet members 51/57/59/61 are around the circumference of the stent 55. However, in alternative embodiment, eyelet members may be only along a narrow section of the stent 55 along the length of the stent 55, as illustrated in FIGS. 14 and 15, as for example, where a seam of the tubular cover 22 is located. FIG. 16 illustrates a perspective view, partially in phantom, of a stent assembly which embodies features of the invention, illustrating a cover 22 secured to the stent 55 by sutures 56 in eyelet members 59 attached to the stent 55. A variety of suitable materials may be used to form the eyelet members including stainless steel, nitinol, and tantalum. In a presently preferred embodiment, the eyelet members are formed of the same material as stent 55. The eyelet members may be formed integral with the stent, or alternatively as a separate member secured thereto, as for example by welding. Preferably, the eyelet members have the same thickness as the stent 55.

The cover 22 is preferably a biocompatible, non-thrombogenic material, such as tissue, PTFE, or DACRON. The thickness of the cover is typically from about 0.07 mm to about 1 mm, and preferably is about 0.1 mm to about 0.4 mm. The cover 22 preferably has a length configured to cover the length of the expanded stent, as illustrated in FIG. 4, showing a stent with a cover 22 extending the length of the stent, with a length equal to the stent length. However, the cover may have a length that is less than or greater than the length of the stent. The cover preferably has a circumference about equal to the circumference of the expanded stent, configured to fit on an inner or outer surface of the expanded stent. The cover preferably fits on the expanded stent so that the cover conforms to the expanded stent without flaps of excess material. The cover may be provided on the unexpanded stent in a folded or overlapping wrapped configuration which provides sufficient material which will unwrap or stretch to cover the larger circumference of the expanded stent.

The cover connectors 13/45 are preferably formed of a metallic material such as stainless steel. However, other resilient materials which are flexible enough to be bendable but stiff enough to hold the bent shape of the closed configuration can be used including platinum or nickel-titanium alloy such as nitinol. Additionally, at least a portion of first section 17 and second section 18 of cover connector 13 may be secured together, as for example by spot welding, after being bent into the closed configuration to secure the cover to the tubular body of the stent.

Stent is typically a metallic material and may comprise a variety of suitable stent designs. For example, in the embodiment where the cover connector is a separate part joined to a stent, a variety of commercially available stents may be used such as Micro Stent II and GFX stents available from Arterial Vascular Engineering, and Multi-Link, available from Guidant. Other stents that may be used in the practice of this invention include the Palmaz-Shatz stent from Johnson and Johnson, the Gianturco stent from Cook Incorporated and other commercially available stents. Conventional balloon expandable stents are preferred, but self-expanding stents, such as those formed from shape memory materials, are also suitable. The length of the stent, for coronary applications, is generally about 4 to greater than about 80 mm, typically about 5 to about 80 mm, preferably about 10 to about 50 mm. The stent generally has a diameter of about 1.5 to about 35 mm, typically about 2 to about 6 mm, preferably about 2.5 to about 5 mm. The actual length and diameter of the stent and cover may vary, and will depend on the nature of the vessel in which the stent assembly is implanted. For example, for peripheral vessel applications, such as an aortic abdominal aneurysm, a larger stent having a length of about 5 mm to about 200 mm and a diameter of about 2 mm to about 60 mm would be used.

Although primarily described with respect to preventing restenosis in angioplasty patients, the covered stents of this invention may be used in a number of coronary artery, peripheral artery and non-vascular applications. For example, coronary artery applications include use in ectatic arteries and ectatic arteries containing an obstructive lesion, aneurismatic arteries, saphenous vein grafts and native arteries, coronary perforation, coronary fistula, and ostial coronary lesions. Peripheral artery applications include aortic abdominal aneurysm and other aneurismatic peripheral arteries, transjugular intrahepatic portal shunt, percutaneous transluminal angioplasty, fistula closing and neuro interventions (such as aneurysms and arterialvenous malformations), small vessel intraluminal grafting, and ostial renal artery lesions. Finally, the covered stents of this invention may be used in urological, gastroenterological, respiratory, neurological, and other non-vascular applications. For example, urological field applications include urethral stenting for stenosis due to tumors, fibrous tissue and perforation. Gastroenterological field applications include fistula closing, reconstruction such as esophagus reconstruction, and esophageal bleeding. Respiratory field applications include tracheal and bronchial obstructions, and neurological field applications include carotid angioplasty.

A general description of the device of the present invention as well as a preferred embodiment of the present invention has been set forth above. One skilled in the art will recognize and be able to practice many changes in many aspects of the device described above, including variations that fall within the teachings of this invention. For example, although the cover is illustrated on the outer surface of the stent, a cover may be secured to an inner surface of the stent using the cover connectors of the invention. Additionally, although the cover is illustrated primarily in terms of a sheet of material forming a cylinder about the stent, the cover connectors may be used to attach a variety of covers to the stent such as ribbons of material wrapped in whole or in part about the stent. The stent assembly may be used in branched body lumens, and positioned to block one or more of the branch lumens or reconstruction of bifurcations by a specially tailored bifurcated cover stent.

What is claimed is:

1. A stent assembly, comprising:
   a) an expandable tubular stent body, which is formed of a plurality of ring sections, having at least one connecting support member extending between adjacent ring sections and which has a cover connecting member with at least two penetrating elements integrally formed with said at least one connecting support member; and
   b) a stent cover which is disposed over at least a portion of said tubular stent body, which is secured to said tubular stent body by said cover connecting member with said at least two penetrating elements extending through said stent cover and extending over an outer surface of said stent cover
wherein a first of said at least two penetrating elements extends through said stent cover at a first location of said stent cover adjacent to a first longitudinal oriented edge of said stent cover and wherein a second of said at least two penetrating elements extends through said stent cover at a second longitudinal oriented location of said stent cover adjacent to a second edge of said stent cover.

2. The stent assembly of claim 1 wherein said stent cover has a cylindrical shape with the first longitudinally oriented edge abutting the second longitudinally oriented edge.

3. The stent assembly of claim 1 wherein said stent cover has a cylindrical shape with the first longitudinally oriented edge overlapping the second longitudinally oriented edge.

4. The stent assembly of claim 1 wherein said stent cover extends from a first end of said stent body to a second end of said stent body.

5. The stent assembly of claim 1 wherein said stent cover is formed of a biocompatible non-thrombogenic material.

6. The stent assembly of claim 1 wherein at least one of said plurality of ring sections at an end of said stent body has undulations and said at least one connecting support member extends between said at least one ring section having undulations and an adjacent ring section.

7. The stent assembly of claim 1 wherein said stent cover further is secured to said stent body by undulations of at least one of said plurality of ring at an end of said stent body which extend over an end portion of said stent cover.

8. The stent assembly of claim 1 having a plurality of connectiong support members extending between adjacent ring sections.

9. A stent assembly, comprising:
   a) an expandable tubular stent body, which is formed of a plurality of ring sections, having at least one connecting support member extending between adjacent ring sections and which has a cover connecting member with at least two penetrating elements integrally formed with said at least one connecting support member; and
   b) a stent cover which is disposed over at least a portion of said tubular stent body, which is secured to said tubular stent body by said cover connecting member with said at least two penetrating elements extending through said stent cover and extending over an outer surface of said stent cover
wherein said stent cover is further secured to said stent body by undulations of at least one of said plurality of ring sections at an end of said stent body which extend over an end portion of said stent cover.

10. The stent assembly of claim 9 wherein said stent cover has a cylindrical shape with a first longitudinally oriented edge abutting a second longitudinally oriented edge.

11. The stent assembly of claim 9 wherein said stent cover has a cylindrical shape with a first longitudinally oriented edge overlapping a second longitudinally oriented edge.

12. The stent assembly of claim 9 wherein said stent cover extends from a first end of said stent body to a second end of said stent body.

13. The stent assembly of claim 9 wherein said stent cover is formed of a biocompatible non-thrombogenic material.

14. The stent assembly of claim 9 wherein at least one of said plurality of ring sections at an end of said stent body has undulations and said at least one said connecting support member extends between said at least one ring section having undulations and an adjacent ring section.

15. The stent assembly of claim 9 having a plurality of connecting support members extending between adjacent ring sections.

* * * * *